(12) United States Patent
Grinvald et al.

(10) Patent No.: US 6,588,901 B1
(45) Date of Patent: Jul. 8, 2003

(54) IMAGING AND ANALYZING MOVEMENT OF INDIVIDUAL ERYTHROCYTES IN BLOOD VESSELS

(75) Inventors: Amiram Grinvald, Rehovot (IL); Darin Nelson, Rehovot (IL)

(73) Assignee: Yeda Research and Development Co., Ltd., Rehovot (IL)

(*) Notice: Subject to any disclaimer, the term of this patent is extended or adjusted under 35 U.S.C. 154(b) by 0 days.

(21) Appl. No.: 09/719,046

(22) PCT Filed: Jun. 7, 1999

(86) PCT No.: PCT/IL99/00303

§ 371 (c)(1),
(2), (4) Date: Jan. 29, 2001

(87) PCT Pub. No.: WO99/63882

PCT Pub. Date: Dec. 16, 1999

(30) Foreign Application Priority Data

Jun. 8, 1998 (IL) .................................. 124814

(51) Int. Cl.[7] .................................................. A61B 3/14
(52) U.S. Cl. ..................................................... 351/206
(58) Field of Search ................................ 351/205, 206, 351/208, 221; 600/407, 310, 317, 322, 323, 437, 452, 453, 318, 320, 476, 479

(56) References Cited

U.S. PATENT DOCUMENTS 5,394,199 A    2/1995  Flower 5,845,639 A  * 12/1998  Hochman et al. ........... 600/407
5,976,502 A  * 11/1999  Khoobehi et al. .......... 600/310

FOREIGN PATENT DOCUMENTS

DE       196 50 117      6/1998
WO       WO 96 17545     6/1996

OTHER PUBLICATIONS

"Reginal Variation in Capillary Hemodynamics in the Cat Retina", Investigative Ophthalmology and Lvisual Science, vol. 39, No. 2, Feb. 1998.

* cited by examiner

Primary Examiner—George Manuel
(74) Attorney, Agent, or Firm—Sughrue Mion, PLLC (57) ABSTRACT

The invention provides a system for directly imaging and analyzing the movement of individual erythrocytes in blood vessels, the system comprising imaging means (4, 26) for acquiring, within a predetermined time interval from each other, at least one pair of images of at least one same erythrocyte for producing at least two frames, each image representing an analog or digital image of the location of the erythrocyte in each of the frames at a predetermined time; image acquisition means (12) for collecting and storing analog or digital images in machine-readable form, and a computer (10) for controlling the operation of the imaging means and the image acquisition means, for processing the at least two frames, and for analyzing the movement of the erythrocyte in the blood vessels. A method for directly imaging and analyzing the movement of individual erythrocytes in blood vessels is also provided.

14 Claims, 6 Drawing Sheets

IMAGING AND ANALYZING MOVEMENT OF INDIVIDUAL ERYTHROCYTES IN BLOOD VESSELS

FIELD OF THE INVENTION

The present invention relates to a system and a method for imaging and analyzing movements of individual erythrocytes in blood vessels. The system and method according to the present invention are particularly useful in imaging and analyzing the movement of erythrocytes in a retina or the head of the optic nerve, facilitating measurement of blood flow.

BACKGROUND OF THE INVENTION

Diseases involving the retinal vasculature are one of the leading causes of blindness worldwide. Many of these diseases are both progressive and treatable. Thus, their early detection is highly desirable. Diagnoses are often made on the basis of the many obvious structural changes which may occur in the retina as a consequence of problems with retinal blood flow. These include neovascularization (the growth of new blood vessels in an attempt to compensate for a reduction in flow through pre-existing vessels), cotton-wool patches (regions in which nerve fiber axoplasmic transport has failed), and eventually the degeneration of retinal nerve fibers. Once observed, these and other phenomena may be used to diagnose retinal vascular disease, and treatment may begin to ameliorate further degeneration. However, it is desirable to detect such problems early, if possible, before irreversible damage has occurred.

For the above reason, attention has focused on developing methods of diagnosing retinal vasculature problems by measuring the rate of retinal blood flow, a reduction in which occurs prior to later, more serious, problems. It is desirable for such a method to be rapid, quantitative, and as non-invasive as possible. Film photography fluorescein and indo-cyanine green (ICG) angiography, for example, are commonly used techniques for assessing retinal blood flow. However, fluorescence angiography is a relatively long procedure (e.g., an hour or more), and is not quantitative, which prohibits assembling a database to which the patient's test results may be readily compared. Fluorescein and ICG angiography require the injection of a large bolus of a fluorescent compound into the bloodstream, a procedure which may have uncomfortable, even dangerous, side effects; and can therefore be administered only when other signs of disease are clearly indicated. Furthermore, only one eye can be carefully followed per injection. Refinement of this technique has improved the quantification of blood flow results, as described in U.S. Pat. Nos. 5,394,199 and 5,437,274, but has retained the disadvantages of invasiveness and, in the case of U.S. Pat. No. 5,394,199, still permits close observation of only one eye.

Another, older, method of measuring retinal blood flow is disclosed in U.S. Pat. No. 4,142,796 and uses the laser Doppler shift effect to detect flow rates at single points. This technique relies on changes in the frequency of light reflected back to a detector from a coherent light source, due to the movement of the target (i.e., blood cells). However, this method does not reveal the overall pattern of blood flow, and so provides only limited information. More recent refinements of this method, disclosed in U.S. Pat. Nos. 5,640,963 and 5,620,000, provide means for moving the laser beam and thus scanning a region of interest, to produce a two-dimensional image. However, use of this technique to date has not found wide acceptance among ophthalmologists, partially because it makes use of an indirect measure of blood flow rates, with uncertain variability in the measurements.

Laser speckle flowgraphy, described in U.S. Pat. Nos. 4,950,070 and 5,090,799, has also been suggested as a means for measuring retinal blood flow. This technique analyzes variations in the reflected light from a laser beam in a small region to determine the rate at which blood is flowing through that region. As for scanning laser Doppler imaging, this technique uses an indirect method to deduce the rate of flow from the signal which is obtained.

Both of the above-described techniques require the use of a laser, a device to scan the laser over the surface of the retina, and a significant number of additional detection optics beyond the basic fundus camera.

Another family of Doppler-effect-based systems is described in U.S. Pat. No. 5,701,898 and relies on shifts in ultrasound frequencies, rather than light frequencies, to determine flow rates. The results, however, are again considered by some ophthalmologists to be difficult to interpret, and do not produce as well-resolved an image as some other techniques.

The common disadvantage of all of the above techniques is that none of them allows the visualization of individual erythrocytes at many sites. Because retinal flow is heterogeneous across different vessels, as well as over a period of time, important diagnostic information may be missed.

The field's interest in, and the importance of, developing a more direct method of measuring retinal blood flow is further illustrated by a technique published in *Investigative Ophthalmology and Visual Science,* Vol. 39, pp. 407–415 (February 1988). This technique is a successful means of directly imaging local blood flow and individual erythrocytes; nevertheless, it is highly invasive, requiring surgical incision of the eye and subsequent introduction of an intraocular endoscope. Its eventual clinical utility is therefore extremely restricted.

Thus, there is a need for a diagnostic device which can measure rates of blood flow in a vessel non-invasively, quantitatively and quickly, and which is straightforward enough in interpretation for find general acceptance among medical practitioners for regular use with patients.

SUMMARY OF THE INVENTION

It is a broad object of the present invention to provide a system and a method for directly and non-invasively measuring blood flow rates in a vessel.

It is a further object of the invention to provide a method for directly, non-invasively measuring blood flow rates in a vessel by detecting the motion of individual erythrocytes in a bloodstream.

A still further object of the present invention is to provide a method for directly, non-invasively measuring blood flow rates by detecting changes in image reflectance of individual erythrocytes in a bloodstream and determining the rate of flow.

In accordance with the present invention, there is therefore provided a system for directly imaging and analyzing the movement of individual erythrocytes in a blood vessel, comprising imaging means for acquiring, within a predetermined time interval from each other, at least one pair of images of at least one same erythrocyte for producing at least two frames, each image representing an analog or digital image of the location of said erythrocyte in each of said frames at a predetermined time; frame grabbing means for collecting and storing said analog or digital images in machine-readable form, and a computer for controlling the operation of said imaging means and said frame grabbing means, for processing said at least two frames, and for analyzing the movement of said erythrocyte in the blood vessel.

The invention further provides a method for directly imaging and analyzing the movement of individual erythrocytes in blood vessels, said method comprising acquiring, within a predetermined time interval from each other, at least one pair of images of at least one same erythrocyte for producing at least two frames, each image representing an analog or digital image of the location of said erythrocyte in each of said frames at a predetermined time; collecting and storing said analog or digital images in machine-readable form and applying said images to a computer to facilitate processing; performing image-difference analysis on said at least two frames to determine a motion signal resulting from the movement of said erythrocyte, and producing a quantitative measurement of the movement of the erythrocyte in said vessels.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

DETAILED DESCRIPTION OF PREFERRED EMBODIMENTS

Figure 1:
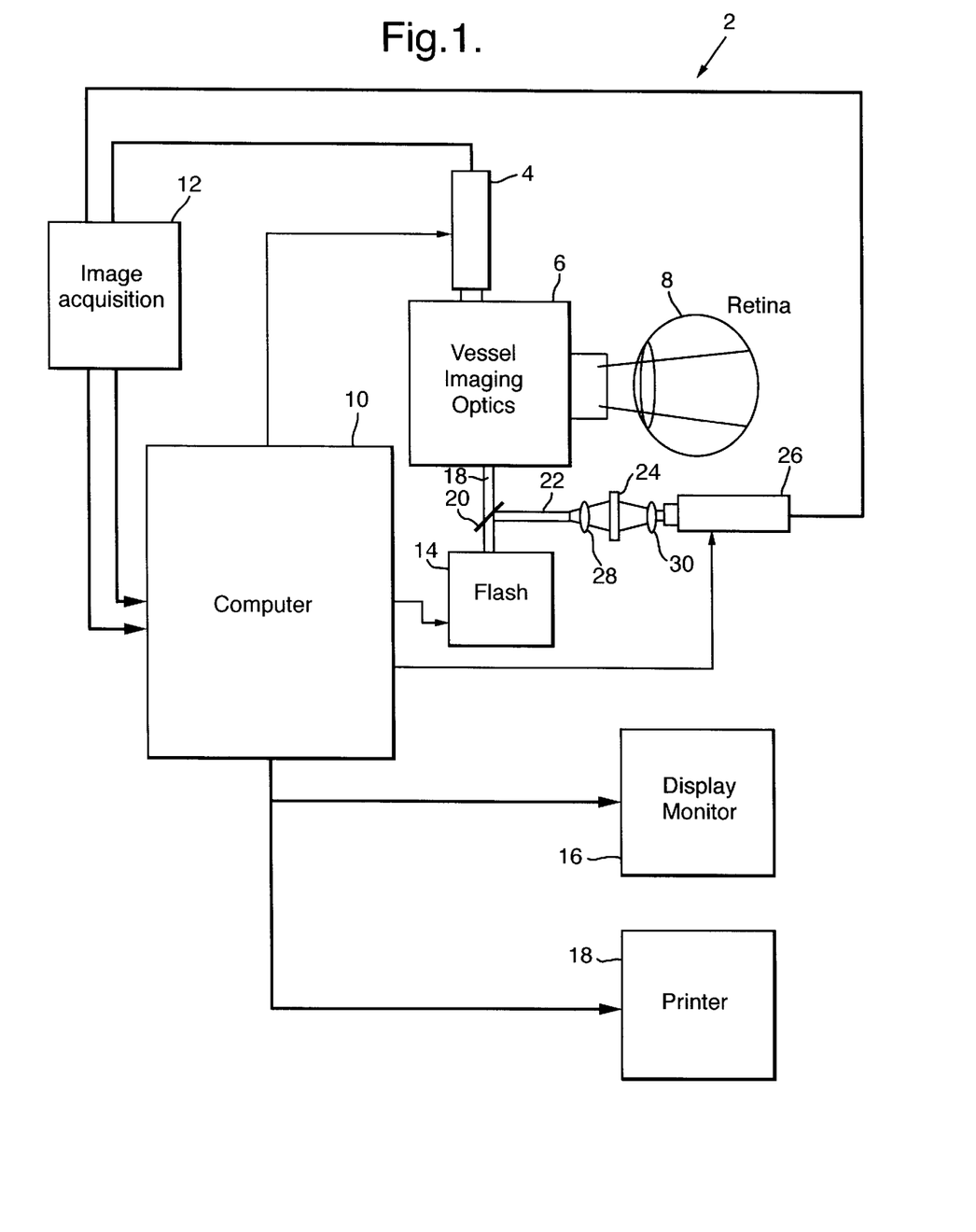
FIG. 1 is a block diagram illustrating the system according to the present invention for non-invasively measuring blood flow rate in a vessel.

In FIG. 1 there is illustrated a preferred embodiment of a system for non-invasively measuring the blood flow rate in a vessel. For illustrative purposes only, the specification relates mainly, as a practical example, to such measurements performed in the retina of an eye. The system 2 includes a good quality (providing at least 10 bits of usable resolution when digitized) imaging means 4, such as a CCD camera in combination with a vessel imaging optical arrangement 6, such as a fundus camera or an ophthalmoscope, viewing the vessels in which measurements are to be performed, in the illustrated case, vessels in retina 8. The imaged data is applied to a computer 10 through an image acquisition interface 12, for example, a digital frame grabber. The computer 10 controls the image acquisition and illumination timing by means of a flash 14 and also has storage capability. There is optionally provided a display monitor 16 for viewing the results of automatic image analysis and permitting interactive image analysis, and a printer 18 for hard copy output of analysis results.

As can be realized, it is important to illuminate the imaged vessel in a closely controlled manner. For each imaged region of vessels to be analyzed, several imaging trials are run. For each trial, two high-resolution, high bit-depth images of the retinal vasculature are obtained within a few msec of one another. The inter-image interval is within the range between 5 and 200 msec, typically between 5 and 100 msec. The interval is varied to aid in extracting slow vs fast motion from both large-diameter and very small-diameter capillaries, venules and arterioles. It is necessary to use brief flashes of light of a few milliseconds or less in order to obtain crisp images. Furthermore, the flashes of light must be nearly identical in intensity, to allow extraction of the motion signal.

An important feature of the invention is the close control of the parameters of illumination of the eye during imaging. Several imaging trials are run for each subject. For each trial, two high-resolution, high bit-depth images of the retinal vasculature are obtained within 5–200 msec of one another (the interval is varied to aid in extracting slow vs fast motion from both large diameter and very small diameter capillaries, venules and arterioles, see below). In order to get crisp images, it is advantageous to use brief flashes of light (a few milliseconds or less); furthermore, the flashes of light must be nearly identical in intensity, to allow extraction of the motion signal. The illumination is advantageously comprised primarily of blue light (400 to 450 nm) and/or green light (530 to 580 nm) to improve the contrast between the erythrocytes, which most strongly absorb in this range, and the relatively reflective retina against which they are imaged. This allows reduction in the overall illumination of the retina.

The above considerations lead to the incorporation of a highly stabilized flash device 14 into the system, with the source of illumination either physically integrated within imaging optical arrangement 6, or attached via a fiber optic lead 18. This flash device is advantageously comprised of a high-powered xenon flash lamp, powered by an externally controlled power supply configured so as to meet the special illumination timing and intensity requirements of the present invention which are not met by the light sources used in previously existing ophthalmic imaging devices. The timing of the flash is controlled by the image acquisition software of computer 10.

The light incident on the retina is passed through a bandpass filter (e.g., 400–450 nm or 530–580 nm) to increase contrast, as described above. While flash illumination has long been used in fundus photography, special emphasis is placed upon brief (5–200 msec) inter-flash intervals, and upon inter-flash stability, both important features of the present invention.

Even when using carefully stabilized illumination sources, irregularities in the image may occur, due to spatial inhomogeneities in the illumination pattern which are not reproduced in each flash. Without additional image information, this type of illumination irregularity cannot be compensated for accurately. The present invention optionally includes means for obtaining this information.

By the use of another beam-splitting element in the illuminating pathway, e.g., partially reflective mirror 20, a fraction of the beam of light used to illuminate the retina is diverted along pathway 22 and brought to impinge on a calibrating target 24 placed at the same image plane as the retina 8. The calibrating target may be an even, white, translucent surface such as ground glass, imaged from behind by a second imaging means 26, such as a video camera with focusing optics 28, 30. The beam splitter element 20 need divert only a small fraction of the overall illumination, because a ground glass target is brighter than the more light-absorbent retina for the same amount of illumination. Furthermore, for a light source with good spectral stability, bandpass filtering need not be applied to the calibration beam (as it is to the retinal illumination beam), further reducing the fraction of total light weight needs to be diverted.

Variations from flash to flash in the image seen by the calibration imaging means 24 are recorded and the information used to provide a correction factor for both overall and spatially localized irregularities in illumination intensity. Back reflections from the calibration target to the retinal imaging camera do not interfere with image acquisition, because they are largely attenuated due to the fractional reflectance of the beam splitter, and because they are subject to the same correction operation as the retina's reflected light.

It should be noted that the calibration imaging means 24 may be relatively inexpensive. It need not have the fine imaging resolution of the retinal imaging means 4, as spatial inhomogeneities in the illumination pattern lack sharp boundaries.

The optics of the vessel-imaging arrangement 6 may be embodied in different ways. As previously described, it can be constituted by a fundus camera for viewing the retina. An ophthalmoscope may provide an alternative means for viewing the retina. The vessel-imaging optics can be embodied by standard camera macro lenses when imaging blood vessels on the surface of the brain, from which the overlying skull and dura have been removed. More generally, an endoscope provides an obvious means for gaining visual access to beds of blood vessels contained within a body. The motion of individual erythrocytes in the bloodstream thus can be detected as small, trackable changes in image reflectance, changes which can be directly analyzed to produce both quantitative and qualitative information as to the rate of flow.

The method of image acquisition and analysis according to the present invention will now be described with reference to FIGS. 2 to 6. In order to assist understanding, reference is first made to FIG. 2, which illustrates a hypothetical image pair (panels A and B) containing a single moving blood cell to be analyzed. In this example, two small circles (representing a moving erythrocyte) can be made out slightly below and to the left of the center of the top two images. In an actual image pair, the single-frame images of the blood cells are completely invisible to the human eye; they are exaggerated here for illustrative purposes.

Figure 2:
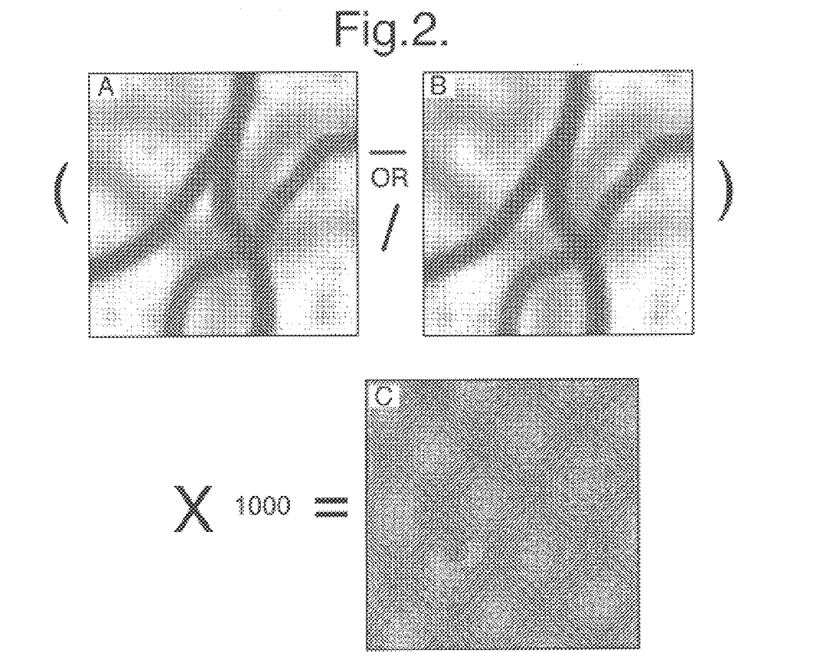
FIG. 2 illustrates the image processing technique.

By subtracting B from A, or dividing A by B, then rescaling the result (multiplying it by a factor of, for example, 100), the differences between the two images are specifically revealed and emphasized. The differences include noise, represented by speckles, but also changes in reflectance due to the movement of the blood cell. The movement of the cell is shown as the dark patch/light patch pair in panel C. Where the patch is dark, the dark-colored blood cell has moved out of its initial (panel A) position; where the image is lighter, it has moved into a new (panel B) position. The region of overlap between the two positions remains encoded as a signal-free gray, as no difference in reflectance is measured at that point.

Obviously, an automated method of motion analysis is desirable, to convert inter-image differences into numbers reflecting the rate of flow. An outline of the strategy used to carry out this analysis follows, with reference to FIG. 3, which illustrates a cluster of erythrocytes in a blood vessel. Seen in panel D is a cluster of erythrocytes moving through a blood vessel BS in the instantaneous direction indicated by the arrow. Obviously, a single blood cell may also be shown; a cluster is depicted only in order to illustrate the generality of the method. Panel E shows the position of these cells a few milliseconds later. For a sufficiently short time interval, the relative placement and rotation of these cells will be similar enough between images to allow their direct comparison. Actual erythrocytes, which are flexible, may also undergo transformations in their shape during their passage through blood vessels.

Figure 3:
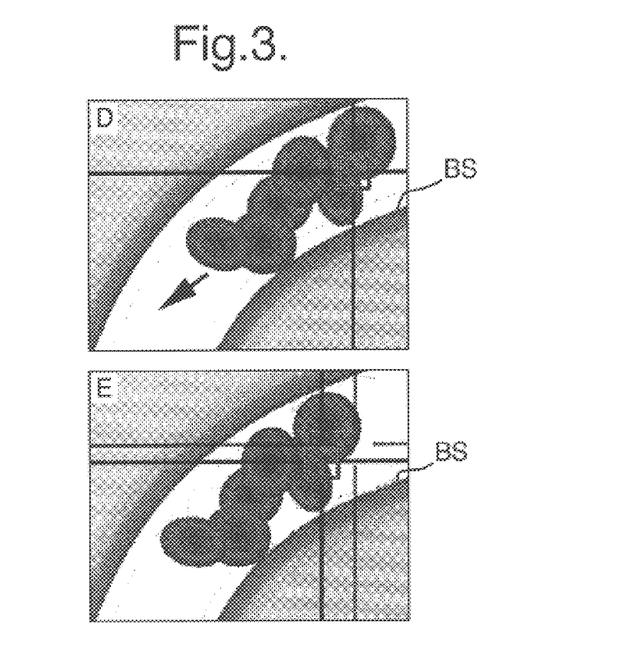
FIG. 3 is a representation of an erythrocyte cluster movement in a blood vessel.

The frame (boxed region) in panel D represents an arbitrary sub-region in the first image, one of many which will be tested automatically. The frame in panel E is in a different location, but the fraction of the overall image it contains is that which most closely matches the frame in panel D. Visually, the similarity is easy to detect; the automated scheme of testing several candidate regions to pick the best match, as described below, is used to perform the same type of matching task.

The displacement of the two frames relative to one another (compare the two sets of cursor lines in panel E), gives the initial estimate of the local direction of motion of blood cells at the region centered on the frame in panel D. Because this method relies only on comparisons between small sub-regions, it does not rely on the overall shape of the groups of blood cells moving through the image, but only on the moment-to-moment similarity in their relative positions as they flow through the vessel.

Figure 4:
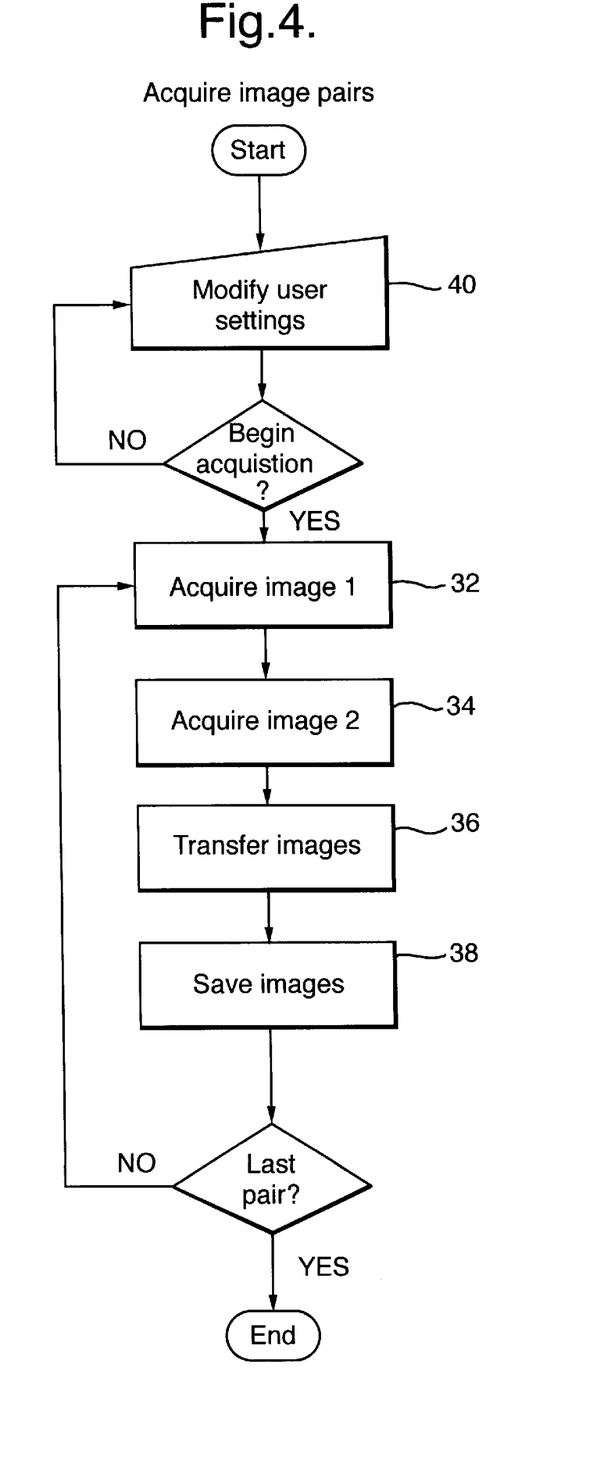
FIG. 4 is a flow diagram illustrating the steps of image acquisition.
Figure 5:
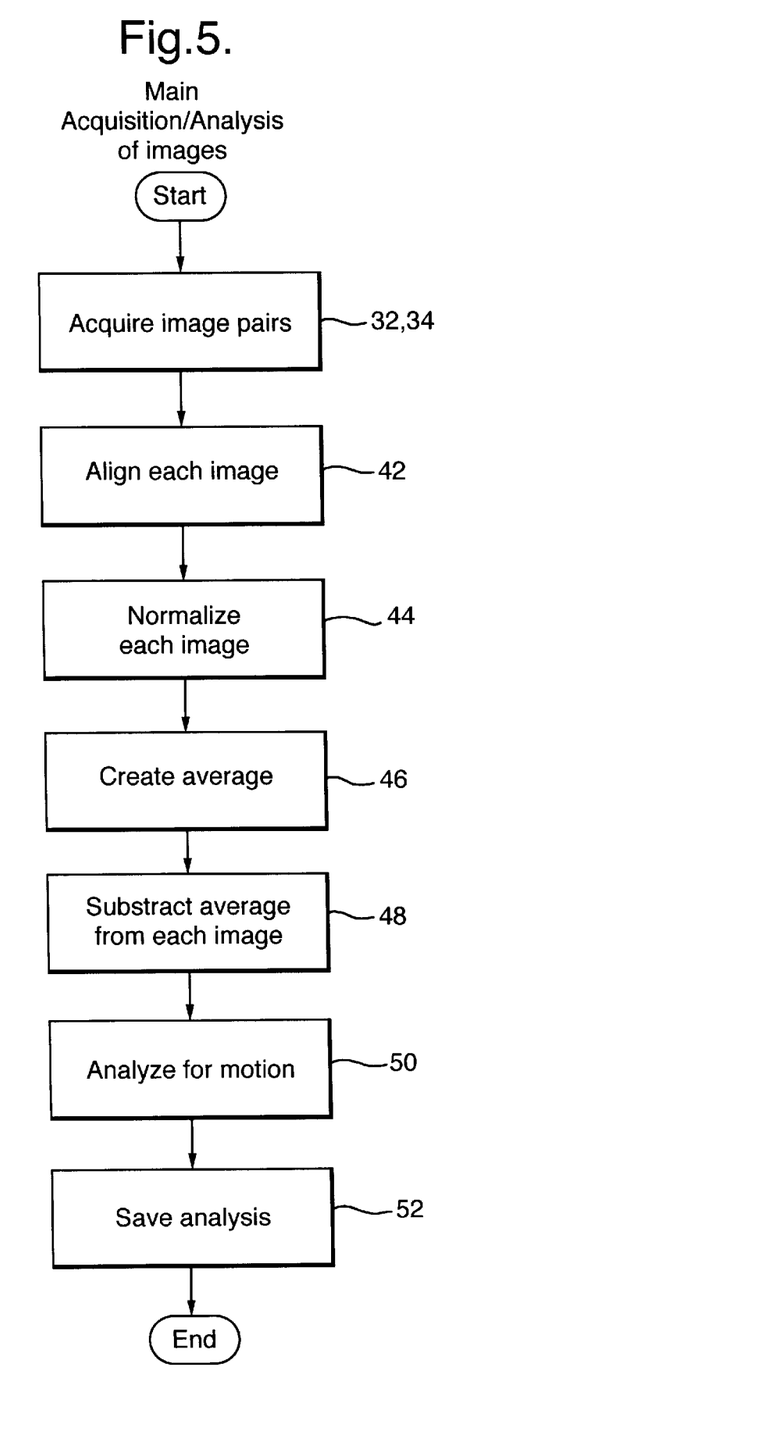
FIG. 5 is a flow diagram illustrating the steps of imaging acquisition, preparatory stages and image processing.

Referring now to FIG. 4, it is seen that during the image acquisition phase of the diagnostic process, many pairs of images can be obtained and stored (steps 32 to 38) with difference inter-image intervals, as determined by the operator at 40. Different rates of flow, such as capillary vs. arteriole, or normal patient vs. anoxic patient, are best detected using different inter-image intervals. Thus, a range of intervals is selected, based on the type of blood vessel to be imaged as well as the operator's expectations, based on previous findings in the patient. A predetermined default range of intervals may, of course, also be used.

Two preferred types of analysis methods are available. One method is entirely automatic once initial parameters have been set by the operator, and converts a set of pairs of acquired images into a single, pseudo-colored image of blood flow rate. The other method provides two displays, which allow the operator to directly view the motion signal using the display monitor 16, supplementing the automated analysis. While the primary object of the present invention is to provide a quantitative report of blood flow rates, providing operators with the ability to qualitatively confirm these results by direct inspection of the acquired images will increase the medical doctor's confidence in the validity of said automatically generated results. In addition, the interpretive power of the human brain and visual system greatly exceeds that of machine vision; thus, permitting direct inspection of the raw motion signal may also produce diagnostic insights which would otherwise be missed, such as, for example, the detection of slowly leaking blood vessels, clumped or misshapen corpuscles, locally and intermittently uneven flow, etc.

Analysis of the images begins substantially identically for both interactive and automatic analyses. In the case of imaging a vessel in a non-stationary organ such as the retina, there are two preparatory steps, shown in FIG. 5: first, global alignment of images at 42 based on the pattern of the vasculature, to correct for any eye movement; and second, image brightness, histogram-based normalization of the images at 44, to correct for small illumination variations which may have occurred. A background blank is constructed at 46 by averaging together many of these images. This background blank is then subtracted from each individual image at 42. The resulting difference image emphasizes the unique features in the low-order bits of the pixels of each image, which are primarily due to the on-going movement of the erythrocytes in the bloodstream. This step performing difference operation is the key to extracting the motion signal available in each image pair for further analyzing the motion at 48 and, if desired, saving the analysis at 50. FIG. 2 illustrates the importance of this step in analyzing the reflectance signal in diagrammatic form. The top two panels A and B show the position of a single erythrocyte, as it might change between two image frames against a stable but complex background. While the round outline of the erythrocyte is not clearly visible in the two raw images, the difference image at bottom panel C does clearly reveal a black-and-white pair of spots, representing the position of the erythrocyte at two points in time.

Clearly, such a difference imaging step might be implemented via alternative algorithms differing in their particulars. One alternative method, which generates substantially the same type of image enhancement, is to divide the two images by one another, which again has the effect of cancelling static information and emphasizing inter-image differences.

Figure 6:
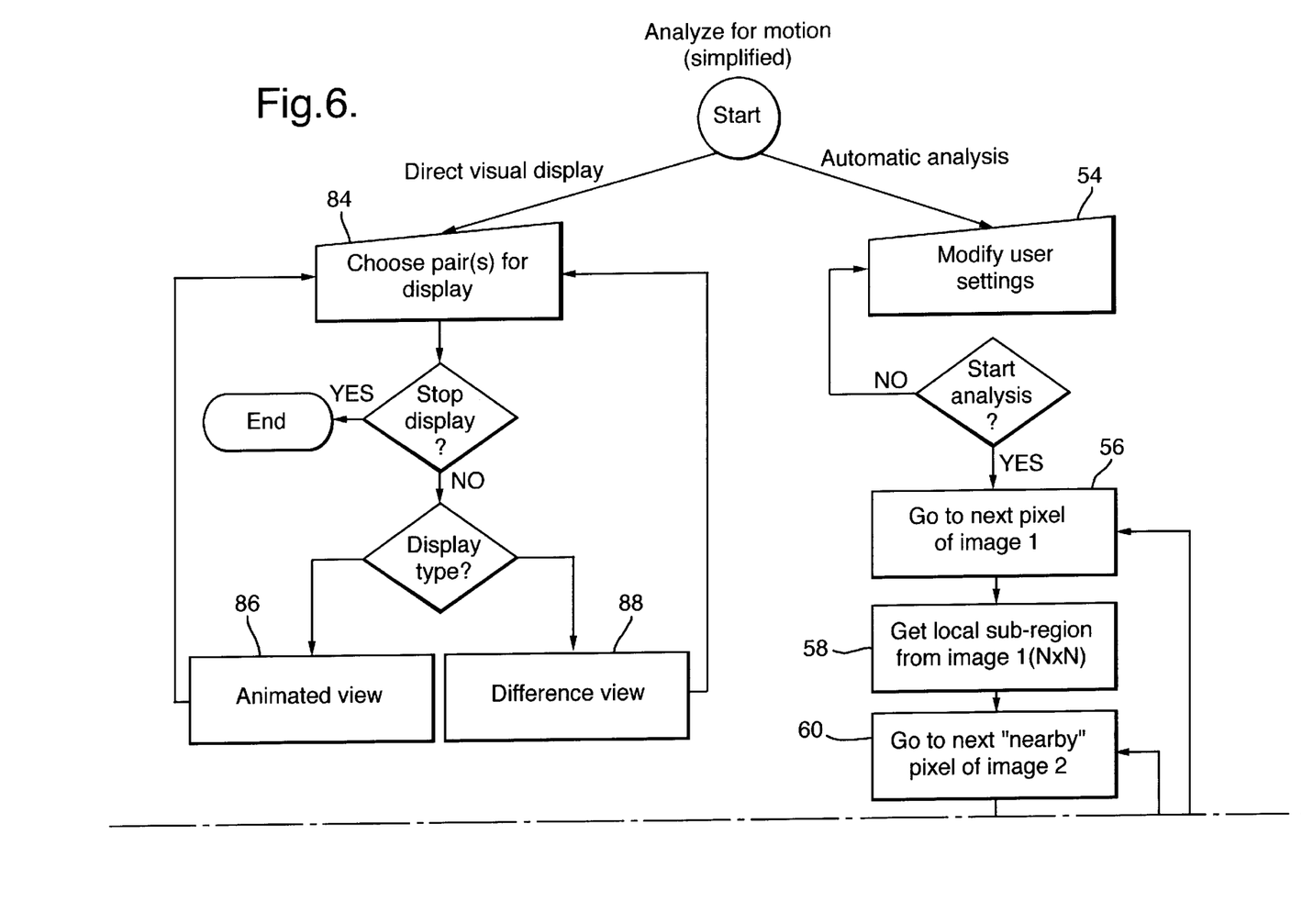
FIG. 6 is a flow diagram of the method according to the present invention, illustrating both automatic and interactive analyses.

Automated motion analysis, based on these difference images, proceeds as shown in FIG. 6. Determination of the direction and rate of flow is begun by comparing small sub-regions of the first image, centered on each pixel in turn, typically 3×3 pixels in size, but changeable by the operator if desired, to many identically-sized, nearby sub-regions of the second image according to steps 52 to 68. By "nearby" is meant within a distance fixed by the operator, typically 10 to 20 pixels. Regions with centers not along the local axis of the vessel, or with motion signals too small for reliable analysis, as determined, e.g., from a threshold image, may optionally be excluded in order to speed processing.

For each pair of sub-regions tested, a number representing their similarity is obtained at 62, fist by squaring the difference between them and then by averaging this value over all the pixels in the difference between the sub-regions. This gives the mean squared error (MSE) between the two sub-regions. Small values represent greater similarity. For the sub-region centered on each pixel in the first image, the relative displacement in two dimensions from the center of each of the M most similar regions from the second image (M may be varied, depending on operator settings) is recorded in rank order at 70.

The results of the foregoing are expected to include a number of errors, including false matches. The next phase of the algorithm 72 to 80 is designed to find the consensus direction and distance of flow (the movement vector) in the local region of the image centered on each pixel. This is done in one preferred instantation by determining the weighted median local displacement of the second image, producing maximum similarity at 76. "Local region", mentioned above, is a user-determined parameter, typically 3×3 or 5×5 pixels. The median determination is weighted by a factor derived from the inverse rank order of the similarity measured for each displacement recorded for each pixel. One obvious extension of this technique would use the average of the movement vectors which fall near the median to estimate the movement vector with sub-pixel precision. Other specific algorithms, trivially varying from the above, may yield substantially the same information; the claim here is the transformation of single-pixel flow estimates into estimates based on the similarity of flow direction among nearby pixels.

Following the above analysis, for each pixel location analyzed, a motion vector is generated at 80, showing how far and in which direction the erythrocytes moved during the inter-image interval.

While the above description refers to the analysis of only a single pair of images, such an analysis is carried out for each of the several image pairs obtained. A map of blood flow direction is compiled from the consensus results obtained by analyzing many such image pairs. By dividing the magnitude of these vectors by the inter-image interval, a rate-of-flow map is created at 82, which may be displayed as a color image. Obviously, this image may itself be subjected to standard image-processing algorithms which perform spatial filtering to reduce noise. Display of this information may also be integrated with information about local blood vessel diameter, computed from a threshold image of the vessel. For example, a graph may be generated, showing optically measured blood flow rate vs. blood vessel diameter, yielding a metric which permits inter-patient comparisons.

Interactive analysis of the images begins from the aligned, normalized images. The operator may view these images in one of two ways: in the first, the averaged image, made from trials acquired, similar to the procedure for the automated analysis, is subtracted from each of a pair of images chosen at 84 by the operator. Again, obviously, more than one pair may be used. These two images are then rapidly and alternately displayed in an on-screen window, the rate being under manual control (animated view 86). The illusion of motion which this provides, allows the operator to visually detect regions of relatively greater and lesser flow rate. The automatically generated quantitative flow rate image may be displayed simultaneously, to verify the qualitative impressions of the operator.

A second qualitative analysis method simply subtracts the second image in a pair from the first at 88. This direct difference image brings out the same motion signal as does average background image subtractions, but compresses it into one image without additional intervening analysis. It produces a static image, mostly gray where there is no change in pixel intensity between images, with dark, negative valued pixels and light, positive valued pixels representing regions from which (dark) and into which (light) erythrocytes have moved during the inter-image interval. This method obviously performs best when the distance moved by the erythrocytes is not too large (on the order of a cell body's width, or less), and when the spacing between individual erythrocytes is relatively clear, as is particularly the case for capillaries. The control of the interval between frames allows the production/selection of the optimal images.

While the analysis algorithm flow chart of FIG. 6, depicts the above-described analysis methods as logically separate branches, it is worthwhile to make switching between the automated and interactive modes of analysis as seamless as possible for the operator, to aid in the understanding of the results. This consideration is implemented in the preferred embodiment of the present invention, wherein the acquisition and analysis software has been designed to permit rapid and flexible movement among pairs of images and among the various views of these images displayed on the computer monitor.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A system for directly imaging and analyzing the movement of individual erythrocytes in blood vessels, said system comprising:

imaging means for acquiring, within a predetermined time interval from each other, at least one pair of images of at least one same erythrocyte for producing at least two frames, each image representing an analog or digital image of the location of said erythrocyte in each of said frames at a predetermined time;

image acquisition means for collecting and storing analog or digital images in machine-readable form, and a computer for controlling the operation of said imaging means and said image acquisition means, for processing said at least two frames and for analyzing the movement of said erythrocyte in said blood vessels;

characterized in that:

said imaging means are non-invasive retinal imaging optics entirely external to the eye, and said computer comprises means for performing image-difference analysis on said frames to determine a motion signal resulting from the movement of said erythrocytes.

2. The system as claimed in claim 1, wherein said imaging means comprises a CCD camera.

3. The system as claimed in claim 1, further comprising a computer-controlled flash for illuminating said erythrocytes upon their being imaged.

4. The system as claimed in claim 3, wherein said computer-controlled flash comprises means for delivering two nearly identical flashes of light sufficiently intense for the motion of retinal erythrocytes to be imaged and detected by said retinal imaging optics, operating in conjunction with said CCD camera, said means being further capable of delivering both of said flashes of light within a time interval of between 5 and 100 milliseconds.

5. The system as claimed in claim 1, further comprising an optical arrangement for detecting variations in the illumination of the erythrocytes during consecutive imaging.

6. The system as claimed in claim 1, further comprising a monitor connected to said computer, for displaying acquired images and processed images and for interactive analysis of the movement of said erythrocytes in blood vessels.

7. The system as claimed in claim 1, further comprising a printer for printing the acquired and processed images.

8. A method for directly imaging and analyzing the movement of individual erythrocytes in blood vessels, said method characterized by:

non-invasively acquiring, within a predetermined time interval from each other, at least one pair of images of at least one same erythrocyte for producing at least two frames, each image representing an analog or digital image of the location of said erythrocyte in each of said frames at a predetermined time;

collecting and storing said analog or digital images in machine-readable form and applying said images to a computer to facilitate processing;

performing image-difference analysis on said at least two frames to determine a motion signal resulting from the movement of said erythrocyte, and producing a quantitative measurement of the movement of the erythrocyte in said vessels.

9. The method as claimed in claim 8, wherein said time interval is between 5 and 100 milliseconds.

10. The method as claimed in claim 8, wherein said image difference analysis is performed by constructing a background blank by averaging together a plurality of frames and subtracting said background blank from each of said at least two frames.

11. The method as claimed in claim 8, further comprising the preparatory step of global alignment of each of said images to correct for movement of the vessels carrying said erythrocytes.

12. The method as claimed in claim 8, further comprising the preparatory step of normalization of the image brightness of said frames to correct small illumination variations between said frames.

13. The method as claimed in claim 8, further comprising illuminating said blood vessels upon acquiring said frames.

14. The method as claimed in claim 8, further comprising the step of displaying said images and an image produced by the motion signal resulting from said image difference analysis, to allow interactive analysis thereof.

* * * * *